US012716852B2

(12) United States Patent
Swain et al.

(10) Patent No.: US 12,716,852 B2
(45) Date of Patent: Aug. 25, 2026

(54) NON-CONTACT METHOD AND SYSTEM FOR INSPECTION AND DETECTION OF WATER SATURATED REGIONS IN ROCKMASS

(71) Applicant: Tata Consultancy Services Limited, Mumbai (IN)

(72) Inventors: Amit Swain, Kolkata (IN); Anwesha Khasnobish, Kolkata (IN); Tapas Chakravarty, Kolkata (IN); Chirabrata Bhaumik, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 285 days.

(21) Appl. No.: 18/744,477

(22) Filed: Jun. 14, 2024

(65) Prior Publication Data

US 2024/0426771 A1 Dec. 26, 2024

(30) Foreign Application Priority Data

Jun. 23, 2023 (IN) ............................ 202321041934

(51) Int. Cl.
*G01N 22/04* (2006.01)
*G01N 33/24* (2006.01)
(Continued)

(52) U.S. Cl.
CPC ........... *G01N 22/04* (2013.01); *G01N 33/246* (2013.01); *G01S 7/295* (2013.01); *G01S 7/41* (2013.01);
(Continued)

(58) Field of Classification Search
CPC .... G01N 22/04; G01N 33/246; G01S 13/885; G01S 13/9021; G01S 13/9027; G01S 7/295; G01S 7/4082; G01S 7/41; G01S 7/412
See application file for complete search history.

(56) References Cited

U.S. PATENT DOCUMENTS

2024/0280689 A1* 8/2024 Tanaka .................... G01S 13/89

FOREIGN PATENT DOCUMENTS

CN 102721965 A 10/2012
CN 111190180 A 5/2020
CN 113126093 A 7/2021

OTHER PUBLICATIONS

Linlin GE et al., "Mine Subsidence Monitoring Using Multi-Source Satellite SAR Images." Photogrammetric Engineering & Remote Sensing, Mar. 2007, American Society for Photogrammetry and Remote Sensing, https://www.ingentaconnect.com/content/asprs/pers/2007/00000073/00000003/art00002:jsessionid=emhc3wzouq4e.x-ic-live-03#.

* cited by examiner

*Primary Examiner* — Timothy A Brainard
(74) *Attorney, Agent, or Firm* — Finnegan, Henderson, Farabow, Garrett & Dunner, LLP

(57) ABSTRACT

Current approaches for detecting water saturated regions in a rockmass uses geophysical methods, such as electrical resistivity tomography (ERT), self-potential (SP), and seismic imaging to spatially detect and map the rock water content in underground mines. However, all these approaches are contact based. Present disclosure provides a non-contact method and system for inspecting and detecting water saturated regions in a rockmass. The system uses coherent radar generated range-compressed data collected from a plurality of rock specimens for generating a gener-
(Continued)

alized calibration function using a range doppler algorithm and a phase tracking algorithm. The system then uses the generated generalized calibration function for estimating water saturation of a target rockmass along with the use of the RDA and the phase tracking algorithm.

12 Claims, 5 Drawing Sheets

(51) Int. Cl.
*G01S 7/295* (2006.01)
*G01S 7/41* (2006.01)
*G01S 13/88* (2006.01)
*G01S 13/90* (2006.01)

(52) U.S. Cl.
CPC ........ *G01S 13/885* (2013.01); *G01S 13/9021* (2019.05)

NON-CONTACT METHOD AND SYSTEM FOR INSPECTION AND DETECTION OF WATER SATURATED REGIONS IN ROCKMASS

PRIORITY CLAIM

This U.S. patent application claims priority under 35 U.S.C. § 119 to: Indian patent application No. 202321041934, filed on 23 Jun. 2023. The entire contents of the aforementioned application are incorporated herein by reference.

TECHNICAL FIELD

The disclosure herein generally relates to water saturation detection, and, more particularly, to a non-contact method and a system for inspection and detection of water saturated regions in a rockmass.

BACKGROUND

Underground mines confront several ground control problems that often lead to roof fall incidents/accidents. In general, the roof fall accidents are considered as most common type of fatality of all the fatalities that occur in coal mines across the globe. These roof fall accidents occur due to multiple reasons, such as weak roof rock, inadequate support, stress conditions, and geological defects. Among these factors, water-related ground control problems are most common in coal mines. Due to rock-water interactions, the mechanical properties of the roof rock deteriorate over time, which ultimately leads to roof rock collapse.

Further, shale or mudstones are the most common roof rocks in coal mines and are extremely moisture sensitive. So, if the shale or mudstone rocks are water saturated for a month, there uniaxial compressive strength (UCS) reduces drastically. This deterioration in the strength of a rockmass is often referred to as water-weakening effect.

Several geophysical approaches like electrical resistivity tomography (ERT), self-potential (SP), and seismic imaging have been attempted in past to spatially map and detect the rock water content in underground galleries. However, all these approaches are contact based thus require physical embedding with the rock-mass for inspection and detection of water saturated regions in the rock-mass.

SUMMARY

Embodiments of the present disclosure present technological improvements as solutions to one or more of the above-mentioned technical problems recognized by the inventors in conventional systems. For example, in one aspect, there is provided a non-contact method and system for inspection and detection of water saturated regions in a rock-mass. The method comprises receiving, by a water saturated region detection system (WSRDS) via one or more hardware processors, a synthetic aperture radar (SAR) data associated with a plurality of rock specimens, wherein the plurality of rock specimens comprises one or more of: a saturated-surface-dried (SSD) rock specimen, an oven-dried (OD) rock specimen and an air-dried (AD) rock specimen; generating, by the WSRDS via the one or more hardware processors, a SAR complex image based on the received SAR data using a range doppler algorithm (RDA), wherein the generated SAR complex image is a two-dimensional (2D) SAR complex image; processing, by the WSRDS via the one or more hardware processors, the 2D SAR complex image using a phase tracking algorithm to obtain a one-dimensional (1D) phase tracking signal, wherein 1D phase tracking signal comprises topography information related to the plurality of rock specimens; estimating, by the WSRDS via the one or more hardware processors, a peak unwrapped phase value for each rock specimen of the plurality of rock specimens based on the 1D phase tracking signal; evaluating, by the WSRDS via the one or more hardware processors, a 3-point empirical polynomial function using the peak unwrapped phase value estimated for each rock specimen of the plurality of rock specimens; and generating, by the WSRDS via the one or more hardware processors, a generalized calibration function for water seepage mapping based, at least in part, on the 3-point empirical polynomial function using a gravimetric water saturation estimation procedure.

In an embodiment, the step of processing, by the WSRDS via the one or more hardware processors, the 2D SAR complex image using the phase tracking algorithm to obtain the 1D phase tracking signal comprises: performing, by the WSRDS via the one or more hardware processors, down-sampling of the 2D SAR complex image along a fast-time dimension by a predefined factor to obtain a down-sampled image; applying, by the WSRDS via the one or more hardware processors, a de-noising filter on the down-sampled image to obtain a de-noised down-sampled image, wherein the de-noised down-sampled image comprises one or more down-sampled signal values; generating, by the WSRDS via the one or more hardware processors, a 1D unwrapped phase tracking signal by taking mean of the one or more down-sampled signal values along the fast-time dimension; and obtaining, by the WSRDS via the one or more hardware processors, the 1D phase tracking signal by applying a bandpass filter on the 1D unwrapped phase tracking signal in a predefined frequency range, wherein the use of the bandpass filter on the 1D unwrapped phase tracking signal ensures that residual noise is removed from the 1D unwrapped phase tracking signal.

In an embodiment, receiving, by the WSRDS via the one or more hardware processors, SAR image data associated with a target rockmass; and estimating, by the WSRDS via the one or more hardware processors, water saturation of the target rockmass using the RDA, the phase tracking algorithm and the generated generalized calibration function, wherein the use of the RDA, the phase tracking algorithm and the generated generalized calibration function ensure that the water saturation of the target rockmass is estimated without contacting the target rockmass.

In an embodiment, the step of estimating, by the WSRDS via the one or more hardware processors, water saturation of the target rockmass using the RDA, the phase tracking algorithm and the generated generalized calibration function comprises: generating, by the WSRDS via the one or more hardware processors, a target SAR complex image based on the received SAR image data using the RDA; reconstructing, by the WSRDS via the one or more hardware processors, a target 1D phase tracking signal using the phase tracking algorithm; computing, by the WSRDS via the one or more hardware processors, a peak unwrapped phase value for the target rockmass based on the target 1D phase tracking signal; and transforming, by the WSRDS via the one or more hardware processors, the peak unwrapped phase value into the water saturation using the generated generalized calibration function.

In another aspect, there is provided a water saturated region detection system for inspection and detection of water saturated regions in a rock-mass. The system comprises a memory storing instructions; one or more communication interfaces; and one or more hardware processors coupled to the memory via the one or more communication interfaces, wherein the one or more hardware processors are configured by the instructions to: receive synthetic aperture radar (SAR) data associated with a plurality of rock specimens, wherein the plurality of rock specimens comprises one or more of: a saturated-surface-dried (SSD) rock specimen, an oven-dried (OD) rock specimen and an air-dried (AD) rock specimen; generate a SAR complex image based on the received SAR data using a range doppler algorithm (RDA), wherein the generated SAR complex image is a two-dimensional (2D) SAR complex image; process the 2D SAR complex image using a phase tracking algorithm to obtain a one-dimensional (1D) phase tracking signal, wherein 1D phase tracking signal comprises topography information related to the plurality of rock specimens; estimate a peak unwrapped phase value for each rock specimen of the plurality of rock specimens based on the 1D phase tracking signal; evaluate a 3-point empirical polynomial function using the peak unwrapped phase value estimated for each rock specimen of the plurality of rock specimens; generate a generalized calibration function for water seepage mapping based, at least in part, on the 3-point empirical polynomial function using a gravimetric water saturation estimation procedure.

In an embodiment, for processing the 2D SAR complex image using the phase tracking algorithm to obtain the 1D phase tracking signal, the one or more hardware processors are configured by the instructions to: perform down-sampling of the 2D SAR complex image along a fast-time dimension by a predefined factor to obtain a down-sampled image; apply a de-noising filter on the down-sampled image to obtain a de-noised down-sampled image, wherein the de-noised down-sampled image comprises one or more down-sampled signal values; generate a 1D unwrapped phase tracking signal by taking mean of the one or more down-sampled signal values along the fast-time dimension; and obtain the 1D phase tracking signal by applying a bandpass filter on the 1D unwrapped phase tracking signal in a predefined frequency range, wherein the use of the bandpass filter on the 1D unwrapped phase tracking signal ensures that residual noise is removed from the 1D unwrapped phase tracking signal.

In an embodiment, receive SAR image data associated with a target rockmass; and estimate water saturation of the target rockmass using the RDA, the phase tracking algorithm and the generated generalized calibration function, wherein the use of the RDA, the phase tracking algorithm and the generated generalized calibration function ensure that the water saturation of the target rockmass is estimated without contacting the target rockmass.

In an embodiment, for estimating water saturation of the target rockmass using the RDA, the phase tracking algorithm and the generated generalized calibration function, the one or more hardware processors are configured by the instructions to: generate a target SAR complex image based on the received SAR image data using the RDA; reconstruct a target 1D phase tracking signal using the phase tracking algorithm; compute a peak unwrapped phase value for the target rockmass based on the target 1D phase tracking signal; and transform the peak unwrapped phase value into the water saturation using the generated generalized calibration function.

In yet another aspect, there are provided one or more non-transitory machine-readable information storage mediums comprising one or more instructions which when executed by one or more hardware processors cause inspection and detection of water saturated regions in a rock-mass by receiving, by a water saturated region detection system (WSRDS), synthetic aperture radar (SAR) data associated with a plurality of rock specimens, wherein the plurality of rock specimens comprises one or more of: a saturated-surface-dried (SSD) rock specimen, an oven-dried (OD) rock specimen and an air-dried (AD) rock specimen; generating, by the WSRDS, a SAR complex image based on the received SAR data using a range doppler algorithm (RDA), wherein the generated SAR complex image is a two-dimensional (2D) SAR complex image; processing, by the WSRDS, the 2D SAR complex image using a phase tracking algorithm to obtain a one-dimensional (1D) phase tracking signal, wherein 1D phase tracking signal comprises topography information related to the plurality of rock specimens; estimating, by the WSRDS, a peak unwrapped phase value for each rock specimen of the plurality of rock specimens based on the 1D phase tracking signal; evaluating, by the WSRDS, a 3-point empirical polynomial function using the peak unwrapped phase value estimated for each rock specimen of the plurality of rock specimens; generating, by the WSRDS, a generalized calibration function for water seepage mapping based, at least in part, on the 3-point empirical polynomial function using a gravimetric water saturation estimation procedure.

In an embodiment, the step of processing, by the WSRDS, the 2D SAR complex image using the phase tracking algorithm to obtain the 1D phase tracking signal comprises: performing, by the WSRDS, down-sampling of the 2D SAR complex image along a fast-time dimension by a predefined factor to obtain a down-sampled image; applying, by the WSRDS, a de-noising filter on the down-sampled image to obtain a de-noised down-sampled image, wherein the de-noised down-sampled image comprises one or more down-sampled signal values; generating, by the WSRDS, a 1D unwrapped phase tracking signal by taking mean of the one or more down-sampled signal values along the fast-time dimension; and obtaining, by the WSRDS, the 1D phase tracking signal by applying a bandpass filter on the 1D unwrapped phase tracking signal in a predefined frequency range, wherein the use of the bandpass filter on the 1D unwrapped phase tracking signal ensures that residual noise is removed from the 1D unwrapped phase tracking signal.

In an embodiment, receiving, by the WSRDS, SAR image data associated with a target rockmass; and estimating, by the WSRDS, water saturation of the target rockmass using the RDA, the phase tracking algorithm and the generated generalized calibration function, wherein the use of the RDA, the phase tracking algorithm and the generated generalized calibration function ensure that the water saturation of the target rockmass is estimated without contacting the target rockmass.

In an embodiment, the step of estimating, by the WSRDS, water saturation of the target rockmass using the RDA, the phase tracking algorithm and the generated generalized calibration function comprises: generating, by the WSRDS, a target SAR complex image based on the received SAR image data using the RDA; reconstructing, by the WSRDS, a target 1D phase tracking signal using the phase tracking algorithm; computing, by the WSRDS, a peak unwrapped phase value for the target rockmass based on the target 1D phase tracking signal; and transforming, by the WSRDS, the peak unwrapped phase value into the water saturation using the generated generalized calibration function.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
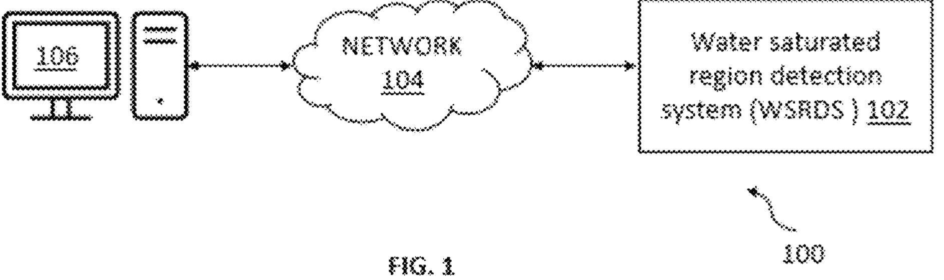
FIG. 1 is an example representation of an environment, related to at least some example embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

As discussed earlier, roof fall accidents are the most common type of accident that happen in coal mines. These accidents sometimes cause serious injuries to workers working in the coal mines. Further, the accidents impact the companies responsible for mining as mining operations gets interrupted due to mine shutdown or equipment breakdown.

These accidents majorly occur due to rock water interactions that leads to weakening of the uniaxial compressive strength (UCS) of the rocks which ultimately results in roof fall accidents.

Some available techniques use geophysical approaches like electrical resistivity tomography (ERT), self-potential (SP), and seismic imaging for detecting water saturation in rocks of coal mines. However, these techniques require physical embedding of receiver array into the rockmass. This can be a risky affair in case of unstable ground conditions.

Thus, there is no known way to perform non-contact inspection and detection of water saturated regions in the rock-mass.

Embodiments of the present disclosure overcome the above-mentioned disadvantages by providing a non-contact method and system for inspection and detection of water saturated regions in a rock-mass. The system of the present disclosure first receives a synthetic aperture radar (SAR) data associated with a plurality of rock specimens. It should be noted that the uncompressed SAR data is obtained by scanning radar on the rock specimens hence no physical contact is made with the rock specimens. Then, the system uses range doppler algorithm (RDA) on the received uncompressed SAR data to obtain complex data/image. Thereafter, the system processes the complex image using a phase tracking algorithm to obtain a one-dimensional (1D) phase tracking signal which is further utilized to generate a generalized calibration function for water seepage mapping. Finally, the system uses the generalized calibration function, the RDA, and the phase tracking algorithm for estimating water saturation of a target rockmass.

In the present disclosure, the system and the method uses millimeter-wave (mm-wave) SAR imaging based technique for water absorption and water saturation detection in a rockmass, thereby ensuring non-contact/contactless water seepage mapping in underground mines.

Referring now to the drawings, and more particularly to FIGS. 1 through 6, where similar reference characters denote corresponding features consistently throughout the figures, there are shown preferred embodiments and these embodiments are described in the context of the following exemplary system and/or method.

FIG. 1 illustrates an exemplary representation of an environment 100 related to at least some example embodiments of the present disclosure. Although the environment 100 is presented in one arrangement, other embodiments may include the parts of the environment 100 (or other parts) arranged otherwise depending on, for example, generating synthetic aperture radar (SAR) complex image, estimating peak unwrapped phase value, etc. The environment 100 generally includes a water saturated region detection system (hereinafter referred as 'WSRDS') 102, and an electronic device 106 (hereinafter also referred as user device 106), each coupled to, and in communication with (and/or with access to) a network 104. It should be noted that one user device is shown for the sake of explanation; there can be more number of user devices.

The network 104 may include, without limitation, a light fidelity (Li-Fi) network, a local area network (LAN), a wide area network (WAN), a metropolitan area network (MAN), a satellite network, the Internet, a fiber optic network, a coaxial cable network, an infrared (IR) network, a radio frequency (RF) network, a virtual network, and/or another suitable public and/or private network capable of supporting communication among two or more of the parts or users illustrated in FIG. 1, or any combination thereof.

Various entities in the environment 100 may connect to the network 104 in accordance with various wired and wireless communication protocols, such as Transmission Control Protocol and Internet Protocol (TCP/IP), User Datagram Protocol (UDP), 2nd Generation (2G), 3rd Generation (3G), 4th Generation (4G), 5th Generation (5G) communication protocols, Long Term Evolution (LTE) communication protocols, or any combination thereof.

The user device 106 is associated with a user who is interested in estimating quality of the unground coal mine or is involved in coal mining. Examples of the user device 106 include, but are not limited to, a personal computer (PC), a mobile phone, a tablet device, a Personal Digital Assistant (PDA), a server, a voice activated assistant, a smartphone, and a laptop.

The water saturated region detection system (hereinafter referred as 'WSRDS') 102 includes one or more hardware processors and a memory. The WSRDS 102 is first configured to receive synthetic aperture radar (SAR) data associated with a plurality of rock specimens via the network 104 from the user device 106. The plurality of rock specimens includes one or more of a saturated-surface-dried (SSD) rock specimen, an oven-dried (OD) rock specimen and an air-dried (AD) rock specimen. The WSRDS 102 then goes into calibration stage where the WSRDS 102 estimates a generalized calibration function for water seepage mapping in a plurality of rock specimens based on the received SAR data using a range doppler algorithm (RDA), phase tracking algorithm and a gravimetric water saturation estimation procedure. Once the generalized calibration function is established, the WSRDS 102 uses it for inspecting the quality of a target rockmass i.e., for mapping water seepage in the target rockmass. The process of calibration and inspection is explained in detail with reference to FIGS. 4 and 5, respectively.

The number and arrangement of systems, devices, and/or networks shown in FIG. 1 are provided as an example. There may be additional systems, devices, and/or networks; fewer systems, devices, and/or networks; different systems, devices, and/or networks; and/or differently arranged systems, devices, and/or networks than those shown in FIG. 1. Furthermore, two or more systems or devices shown in FIG. 1 may be implemented within a single system or device, or a single system or device shown in FIG. 1 may be implemented as multiple, distributed systems or devices. Additionally, or alternatively, a set of systems (e.g., one or more systems) or a set of devices (e.g., one or more devices) of the environment 100 may perform one or more functions described as being performed by another set of systems or another set of devices of the environment 100 (e.g., refer scenarios described above).

Figure 2:
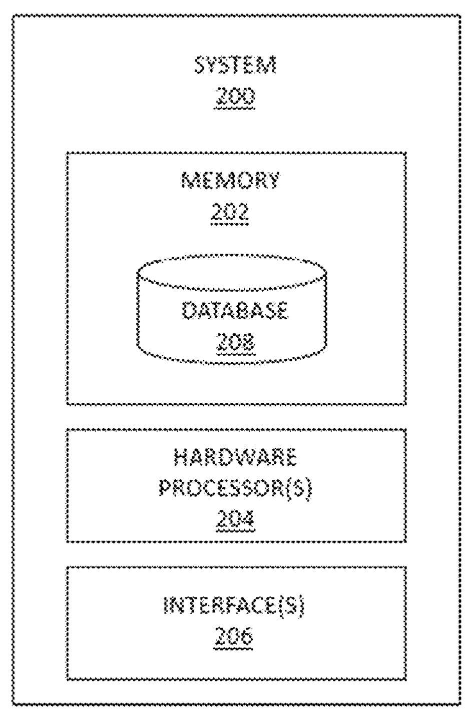
FIG. 2 illustrates an exemplary block diagram of a system for inspection and detection of water saturated regions in a rock-mass, in accordance with an embodiment of the present disclosure.

FIG. 2 illustrates an exemplary block diagram of a water saturated region detection system 200 for inspection and detection of water saturated regions in a rock-mass, in accordance with an embodiment of the present disclosure. In an embodiment, the water saturated region detection system 200 may also be referred as system 200 and may be interchangeably used herein. The water saturated region detection system 200 is similar to the WSRDS 102 explained with reference to FIG. 1. In some embodiments, the system 200 is embodied as a cloud-based and/or SaaS-based (software as a service) architecture. In some embodiments, the system 200 may be implemented in a server system. In some embodiments, the system 200 may be implemented in a variety of computing systems, such as laptop computers, notebooks, hand-held devices, workstations, mainframe computers, and the like.

In an embodiment, the system 200 includes one or more processors 204, communication interface device(s) or input/output (I/O) interface(s) 206, and one or more data storage devices or memory 202 operatively coupled to the one or more processors 204. The one or more processors 204 may be one or more software processing modules and/or hardware processors. In an embodiment, the hardware processors can be implemented microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 200 can be implemented in a variety of computing systems, such as laptop computers, notebooks, hand-held devices, workstations, mainframe computers, servers, a network cloud and the like.

The I/O interface device(s) 206 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 208 can be stored in the memory 202, wherein the database 208 may comprise, but are not limited to, generalized calibration function, a phase tracking algorithm, and the like. The memory 202 further comprises (or may further comprise) information pertaining to input(s)/output(s) of each step performed by the systems and methods of the present disclosure. In other words, input(s) fed at each step and output(s) generated at each step are comprised in the memory 202 and can be utilized in further processing and analysis.

It is noted that the system 200 as illustrated and hereinafter described is merely illustrative of an apparatus that could benefit from embodiments of the present disclosure and, therefore, should not be taken to limit the scope of the present disclosure. It is noted that the system 200 may include fewer or more components than those depicted in FIG. 2.

Figure 3:
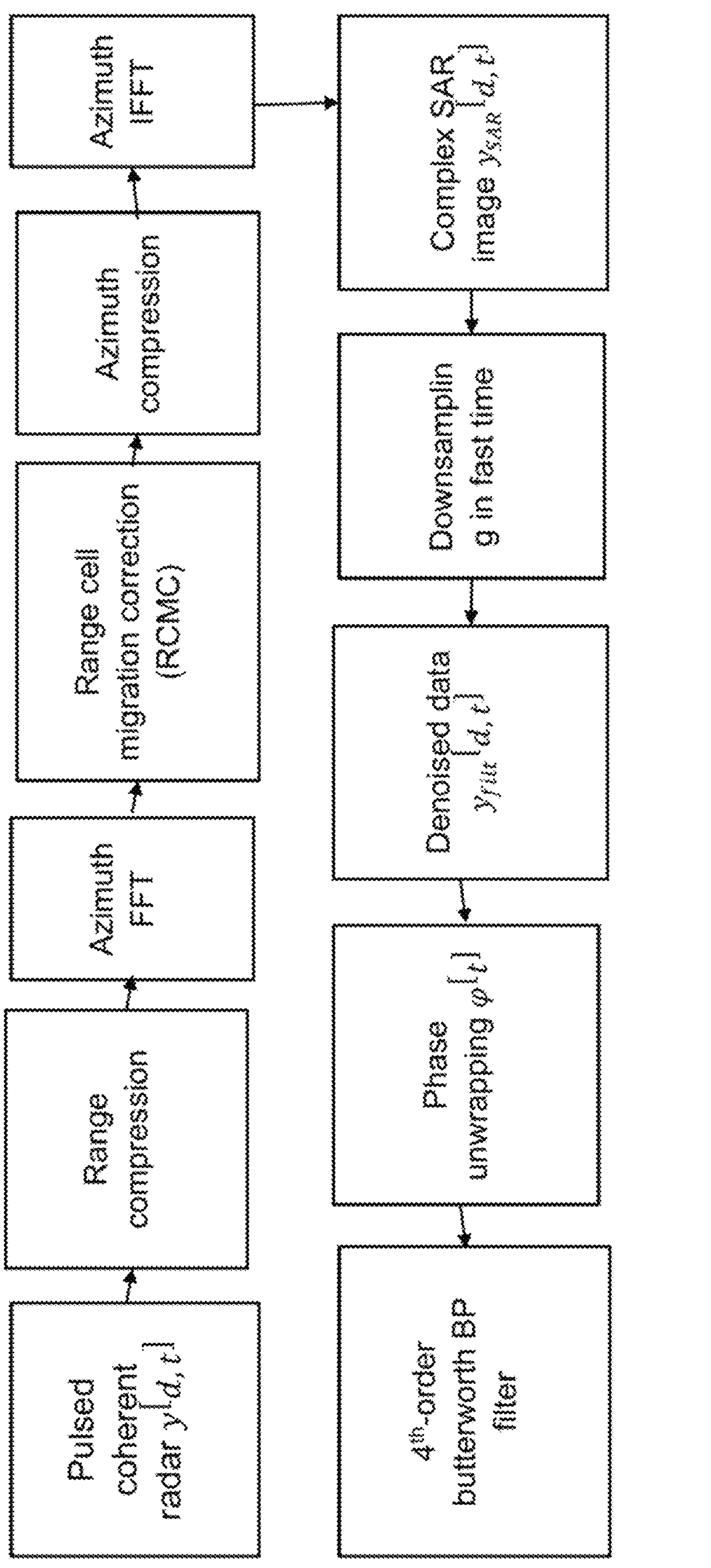
FIG. 3 illustrates a schematic block diagram representation of a process associated with the system of FIG. 2, for obtaining a one dimensional phase tracking signal, in accordance with an embodiment of the present disclosure.

FIG. 3, with reference to FIGS. 1-2, illustrates a schematic block diagram representation 300 of a process associated with the system 200 of FIG. 2 or the WSRDS 102 of FIG. 1 for obtaining the 1D phase tracking signal, in accordance with an embodiment of the present disclosure.

As seen in FIG. 3, the system 200 first receives a pulsed coherent radar data i.e., the SAR data associated with a plurality of rock specimens. The system then uses a range doppler algorithm to generate a SAR complex image based on the received SAR data. In the range doppler algorithm, first range compression is performed on the SAR data. Then, Fast Fourier transforms (FFT) is performed in azimuth direction on the range compressed data. Thereafter, range cell migration correction, azimuth compression and inverse FFTs are performed to generate the SAR complex image. The generated SAR complex image is a two-dimensional (2D) SAR complex image. So, the system 200 performs down sampling of the 2D SAR complex image along a fast-time dimension by a predefined factor to obtain a down-sampled image. Then, the system 200 applies a denoising low-pass filter on the down-sampled image to obtain a denoised down-sampled image.

Thereafter, the system 200 performs phase unwrapping. In phase unwrapping, a 1D unwrapped phase tracking signal is generated by taking mean of the one or more down-sampled signal values along the fast-time dimension.

Finally, the system applies a 4th order band-pass filter on the 1D unwrapped phase tracking signal to obtain the 1D phase tracking signal.

Figure 4:
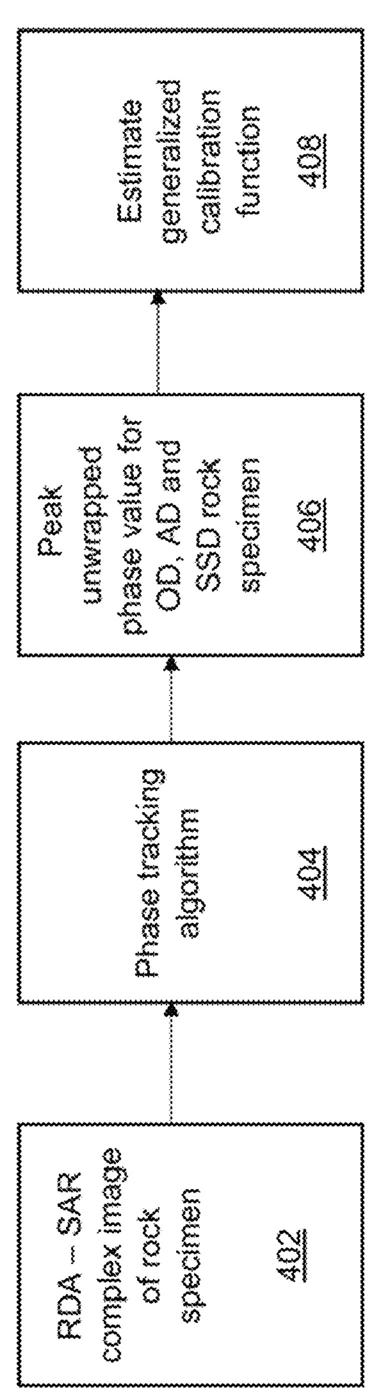
FIG. 4 illustrates a calibration process associated with the system of FIG. 2, for generating a generalized calibration function for water seepage mapping, in accordance with an embodiment of the present disclosure.

FIG. 4, with reference to FIGS. 1-3, illustrates a schematic block diagram representation 300 of a calibration process associated with the system 200 of FIG. 2 or the WSRDS 102 of FIG. 1 for generating a generalized calibration function for water seepage mapping, in accordance with an embodiment of the present disclosure.

It should be noted that the system 200 first receives the SAR data associated with a plurality of rock specimens i.e., the SAR data of OD, AD and SSD rock specimens are collected as an input which is then processed to generate the generalized calibration function.

At 402, a SAR complex image is generated for the rock specimens based on the SAR data of the rock specimens using a range doppler algorithm. In particular, the range doppler algorithm is executed on radar backscatter data y[d, t] of rock specimens to generate SAR complex image $y_{SAR}$[d, t]. The SAR complex image is a 2D SAR complex image.

At 404, a phase tracking algorithm is used to process the 2D SAR complex image to obtain a 1D phase tracking signal. In particular, the SAR phase tracking algorithm is used to derive a low-noise unwrapped phase tracking signal from the 2D SAR complex image. The 1D phase tracking signal includes topography information related to a rockmass under test. The above step can be better understood by way of following description.

The 2D SAR complex image generated by the RDA is first down-sampled along the fast-time dimension by a factor D (d1=d/D) to obtain a down-sampled image. Then, a denoising filter with heuristically determined filter co-efficient is applied to obtain a de-noised down-sampled image. In an embodiment, the de-noised down-sampled image comprises one or more down-sampled signal values.

$$y_{filt}[d1, t] = \alpha_i y_{filt}[d1, t-1] + (1-\alpha_i) y_{SAR}[d1, t],$$

Where, $y_{filt}$[d1, t] is the de-noised, down-sampled image, $y_{SAR}$[d1, t] is the down-sampled SAR complex image, $f_s$ is the sweep frequency, $\tau$ is the time constant, and $\alpha_i = \exp(-2/\tau f_s)$ is the low-pass filter factor.

As the signal values, even after applying the denoising filter, are in between $-\pi$ to $\pi$ and not as a continuous signal, the signal-values are unwrapped to generate a 1D unwrapped phase tracking signal. In unwrapping, a mean of the down-sampled signal values is taken along the fast-time values to generate the 1D unwrapped phase signal:

$$\varphi[t] = \alpha_\varphi \varphi[t-1] + L\left\{\sum_{d=1}^{L-1} y_{filt}[d1, t] \times \overline{y}_{filt}[d1, t-1]\right],$$

Where, $\alpha_\varphi$ is the high-pass filter factor $$\left(\alpha_\varphi = \exp\left(-\frac{2f_i}{f_s}\right)\right),$$

$f_i$ is the lowest frequency of interest for the filter,

L is the number of fast time samples, and $\overline{y}_{filt}$ is the complex conjugate of $y_{filt}$.

Further, to reconstruct a final output phase, a 4th order Butterworth bandpass filter is applied to remove any residual noise. In an embodiment, without limiting the scope of the embodiments disclosed herein, the bandpass filter is applied in the frequency range of 0.1-5 Hz.

At 406, a peak unwrapped phase value is estimated for each rock specimen of the plurality of rock specimens based on the 1D phase tracking signal. The estimated phase values are represented by $\phi_{dry}$, $\phi_{ssd}$ and $\phi_{air\text{-}dried}$.

At 408, the three peak unwrapped phase values $\phi_{dry}$, $\phi_{ssd}$ and $\phi_{air\text{-}dried}$ are used to evaluate a 3-point polynomial function. In which, $\phi_{dry}$ corresponds to peak unwrapped phase at zero level of water saturation, and $\phi_{ssd}$ and $\phi_{air\text{-}dried}$ represent peak unwrapped phase at higher and medium values of water saturation. In an embodiment, the 3-point polynomial function is evaluated so that correctness of the water seepage mapping is established while inspecting the spatial variation of water saturation along the stretch of a rockmass.

$$A = A_{dry} + \frac{\phi - \phi_{dry}}{2}\left(\frac{A_{ssd} - A_{dry}}{\phi_{ssd} - \phi_{dry}} + \frac{A_{ad} - A_{dry}}{\phi_{ad} - \phi_{dry}}\right)$$

For oven-dried sample, $A_{dry}$=0, so $$A = \frac{\phi - \phi_{dry}}{2}\left(\frac{A_{ssd}}{\phi_{ssd} - \phi_{dry}} + \frac{A_{ad}}{\phi_{ad} - \phi_{dry}}\right)$$

Further, if m number of 'ssd' observations and n number of 'ad' observations are used, then $$A = \frac{\phi - \phi_{dry}}{2m}\left(\sum_{i=1}^{m} \frac{(A_{ssd})_i}{(\phi_{ssd})_i - \phi_{dry}}\right) + \frac{\phi - \phi_{dry}}{2n}\left(\sum_{j=1}^{n} \frac{(A_{ad})_j}{(\phi_{ad})_j - \phi_{dry}}\right)$$

where, A is the estimated water saturation of the rockmass under study, $A_{ssd}$ is the experimentally determined water saturation for the saturated surface dried rock specimen, $A_{ad}$ is the experimentally determined water saturation for the air-dried rock specimen, $\phi$ is the peak unwrapped phase value from the reconstructed phase tracking signal, $\phi_{dry}$ is the experimentally determined peak unwrapped phase value for the dry rock specimen, $\phi_{ssd}$ is the experimentally determined peak unwrapped phase value for the saturated surface dried rock specimen, and $\phi_{ad}$ is the experimentally determined peak unwrapped phase value for the air-dried rock specimen, m is the number of saturated surface dried specimen observations, and n is the number of air dried specimen observations.

It should be noted that the 'm' and 'n' may correspond to a plurality of observations taken from different or even same rock type, thereby making the calibration function more generalized and rock-type agnostic.

The 3-point polynomial function is then used to generate a generalized calibration function for water seepage mapping on actual rockmass with fixed standoff distance. It should be noted that the actual water saturation is measured using gravimetric water saturation estimation procedure provided under American society for testing and materials (ASTM) guidelines.

Figure 5:
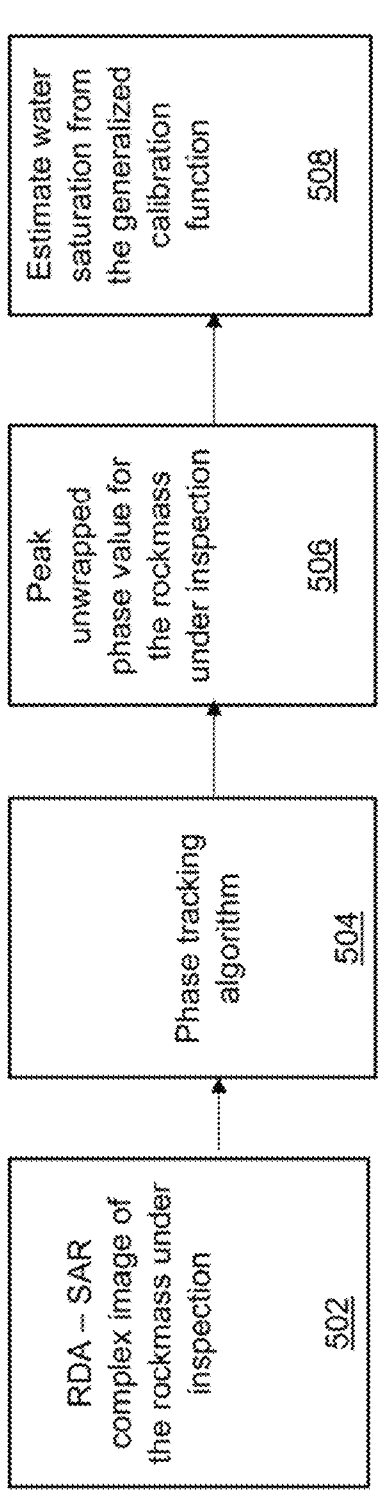
FIG. 5 illustrates an inspection process for estimating water saturation of a target rockmass using the generalized calibration function, in accordance with an embodiment of the present disclosure.

FIG. 5, with reference to FIGS. 1-4, illustrates a schematic block diagram representation 300 of an inspection process associated with the system 200 of FIG. 2 or the WSRDS 102 of FIG. 1 for estimating water saturation of a target rockmass using the generalized calibration function, in accordance with an embodiment of the present disclosure.

It should be noted that the system 200 first receives an SAR image data associated with a target rockmass.

At 502, a target SAR complex image $y_{SAR}[d, t]$ is generated based on the received SAR image data y[d, t] using the RDA.

At 504, a target 1D phase tracking signal is reconstructed using the phase tracking algorithm.

At 506, a peak unwrapped phase value for the target rockmass is computed based on the target 1D phase tracking signal.

At 508, water saturation is estimated using the generalized calibration function. In particular, the peak unwrapped phase value is transformed to water saturation using the generalized calibration function.

Figure 6:
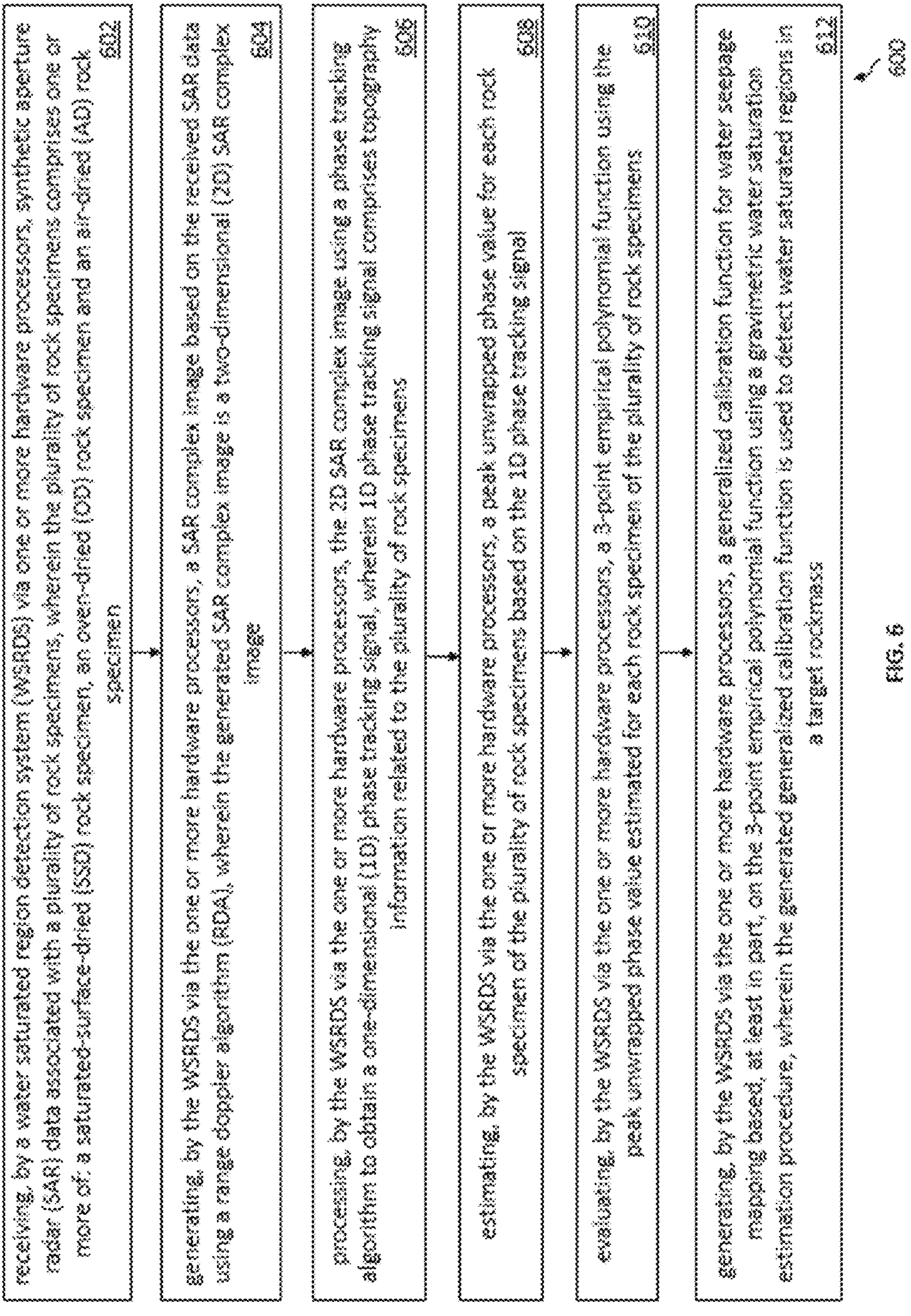
FIG. 6 illustrates an exemplary flow diagram of a method for inspection and detection of water saturated regions in a rock-mass, using the system of FIG. 2, in accordance with an embodiment of the present disclosure.

FIG. 6, with reference to FIGS. 1 through 5 represent an exemplary flow diagram of a method 400 for inspecting and detecting water saturated regions in a rock-mass, in accordance with an embodiment of the present disclosure. The method 600 may use the system 200 of FIG. 2 and WSRDS 102 of FIG. 1 for execution. In an embodiment, the system 200 comprises one or more data storage devices or the memory 202 operatively coupled to the one or more hardware processors 204 and is configured to store instructions for execution of steps of the method 600 by the one or more hardware processors 204. The sequence of steps of the flow diagram may not be necessarily executed in the same order as they are presented. Further, one or more steps may be grouped together and performed in form of a single step, or one step may have several sub-steps that may be performed in parallel or in sequential manner. The steps of the method 600 of the present disclosure will now be explained with reference to the components of the system 200 as depicted in FIG. 2, and the WSRDS 102 of FIG. 1.

At step 602 of the method of the present disclosure, the one or more hardware processors 204 of the system 200 receive the synthetic aperture radar (SAR) data associated with a plurality of rock specimens. The plurality of rock specimens include one or more of: a saturated-surface-dried (SSD) rock specimen, an oven-dried (OD) rock specimen and an air-dried (AD) rock specimen.

At step 604 of the method of the present disclosure, the one or more hardware processors 204 of the system 200 generate a SAR complex image based on the received SAR data using an RDA. In an embodiment, the generated SAR complex image is a two-dimensional (2D) SAR complex image. The process of generating the SAR complex image using the RDA is already explained with reference to FIG. 3 and is not herein explained for the sake of brevity.

At step 606 of the present disclosure, the one or more hardware processors 204 of the system 200 process the 2D SAR complex image using a phase tracking algorithm to obtain a one-dimensional (1D) phase tracking signal. The process of obtaining the one-dimensional (1D) phase tracking signal using the phase tracking algorithm is already explained with reference to FIG. 3 and is not herein explained for the sake of brevity.

At step 608 of the method of the present disclosure, the one or more hardware processors 204 of the system 200 estimate a peak unwrapped phase value for each rock specimen of the plurality of rock specimens based on the 1D phase tracking signal.

At step 610 of the method of the present disclosure, the one or more hardware processors 204 of the system 200 evaluate a 3-point empirical polynomial function using the peak unwrapped phase value estimated for each rock specimen of the plurality of rock specimens. The process of evaluating is explained in detail with reference to FIG. 4 and is not herein explained for the sake of brevity.

At step 612 of the method of the present disclosure, the one or more hardware processors 204 of the system 200 generate a generalized calibration function for water seepage mapping based, at least in part, on the 3-point empirical polynomial function using a gravimetric water saturation estimation procedure.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

As discussed earlier, major challenges faced by underground mines are roof fall incidents. Accidents occur due to weak roof rock, inadequate support, stress conditions, and geological defects. Among these factors, water-related ground control problems are most common in coal mines. Due to rock-water interactions, the mechanical properties of the roof rock deteriorate over time, inevitably leading to collapse. Few approaches that are available for inspection and detection of water saturated regions are contact based which involves the risk of accidents. So, to overcome the disadvantages, embodiments of the present disclosure provide a method and a system for inspecting and detecting water saturated regions in a rock-mass. More specifically, the system and the method leverages millimeter-wave (mm-wave) synthetic aperture radar imaging based technique, thereby ensuring non-contact/contactless water seepage mapping in underground mines.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:

receiving, by a water saturated region detection system (WSRDS) via one or more hardware processors, a synthetic aperture radar (SAR) data associated with a plurality of rock specimens, wherein the plurality of rock specimens comprises one or more of: a saturated-surface-dried (SSD) rock specimen, an oven-dried (OD) rock specimen, and an air-dried (AD) rock specimen;

generating, by the WSRDS via the one or more hardware processors, a SAR complex image based on the received SAR data using a range doppler algorithm (RDA), wherein the generated SAR complex image is a two-dimensional (2D) SAR complex image;

processing, by the WSRDS via the one or more hardware processors, the 2D SAR complex image using a phase tracking algorithm to obtain a one-dimensional (1D) phase tracking signal, wherein 1D phase tracking signal comprises topography information related to the plurality of rock specimens;

estimating, by the WSRDS via the one or more hardware processors, a peak unwrapped phase value for each rock specimen of the plurality of rock specimens based on the 1D phase tracking signal;

evaluating, by the WSRDS via the one or more hardware processors, a 3-point empirical polynomial function using the peak unwrapped phase value estimated for each rock specimen of the plurality of rock specimens; and generating, by the WSRDS via the one or more hardware processors, a generalized calibration function for water seepage mapping based, at least in part, on the 3-point empirical polynomial function using a gravimetric water saturation estimation procedure, wherein the generated generalized calibration function is used to detect water saturated regions in a target rockmass.

2. The processor implemented method of claim 1, wherein the step of processing, by the WSRDS via the one or more hardware processors, the 2D SAR complex image using the phase tracking algorithm to obtain the 1D phase tracking signal comprises:

performing down-sampling of the 2D SAR complex image along a fast-time dimension by a predefined factor to obtain a down-sampled image;

applying a de-noising filter on the down-sampled image to obtain a de-noised down-sampled image, wherein the de-noised down-sampled image comprises one or more down-sampled signal values;

generating a 1D unwrapped phase tracking signal by taking mean of the one or more down-sampled signal values along the fast-time dimension; and obtaining the 1D phase tracking signal by applying a bandpass filter on the 1D unwrapped phase tracking signal in a predefined frequency range, wherein the use of the bandpass filter on the 1D unwrapped phase tracking signal ensures that residual noise is removed from the 1D unwrapped phase tracking signal.

3. The processor implemented method of claim 1, further comprising:

receiving, by the WSRDS via the one or more hardware processors, SAR image data associated with a target rockmass; and estimating, by the WSRDS via the one or more hardware processors, water saturation of the target rockmass using the RDA, the phase tracking algorithm and the generated generalized calibration function, wherein the use of the RDA, the phase tracking algorithm, and the generated generalized calibration function ensure that the water saturation of the target rockmass is estimated without contacting the target rockmass.

4. The processor implemented method of claim 3, wherein the step of estimating, by the WSRDS via the one or more hardware processors, the water saturation of the target rockmass using the RDA, the phase tracking algorithm and the generated generalized calibration function, comprises:

generating a target SAR complex image based on the received SAR image data using the RDA;

reconstructing a target 1D phase tracking signal using the phase tracking algorithm;

computing a peak unwrapped phase value for the target rockmass based on the target 1D phase tracking signal; and transforming the peak unwrapped phase value into the water saturation using the generated generalized calibration function.

5. A water saturated region detection system, comprising:

a memory storing instructions;

one or more communication interfaces; and one or more hardware processors coupled to the memory via the one or more communication interfaces, wherein the one or more hardware processors are configured by the instructions to:

receive a synthetic aperture radar (SAR) data associated with a plurality of rock specimens, wherein the plurality of rock specimens comprises one or more of: a saturated-surface-dried (SSD) rock specimen, an oven-dried (OD) rock specimen, and an air-dried (AD) rock specimen;

generate a SAR complex image based on the received SAR data using a range doppler algorithm (RDA), wherein the generated SAR complex image is a two-dimensional (2D) SAR complex image;

process the 2D SAR complex image using a phase tracking algorithm to obtain a one-dimensional (1D) phase tracking signal, wherein 1D phase tracking signal comprises topography information related to the plurality of rock specimens;

estimate a peak unwrapped phase value for each rock specimen of the plurality of rock specimens based on the 1D phase tracking signal;

evaluate a 3-point empirical polynomial function using the peak unwrapped phase value estimated for each rock specimen of the plurality of rock specimens;

generate a generalized calibration function for water seepage mapping based, at least in part, on the 3-point empirical polynomial function using a gravimetric water saturation estimation procedure;

receiving SAR image data associated with a target rockmass; and estimate water saturation of the target rockmass using the RDA, the phase tracking algorithm and the generated generalized calibration function, wherein the use of the RDA, the phase tracking algorithm and the generated generalized calibration function ensure that the water saturation of the target rockmass is estimated without contacting the target rockmass.

6. The water saturated region detection system of claim 5, wherein for processing the 2D SAR complex image using the phase tracking algorithm to obtain the 1D phase tracking signal, the one or more hardware processors) are configured by the instructions to:

perform down-sampling of the 2D SAR complex image along a fast-time dimension by a predefined factor to obtain a down-sampled image;

apply a de-noising filter on the down-sampled image to obtain a de-noised down-sampled image, wherein the de-noised down-sampled image comprises one or more down-sampled signal values;

generate a 1D unwrapped phase tracking signal by taking mean of the one or more down-sampled signal values along the fast-time dimension; and obtain the 1D phase tracking signal by applying a bandpass filter on the 1D unwrapped phase tracking signal in a predefined frequency range, wherein the use of the bandpass filter on the 1D unwrapped phase tracking signal ensures that residual noise is removed from the 1D unwrapped phase tracking signal.

7. The water saturated region detection system of claim 5, wherein the one or more hardware processors are configured by the instructions to:

receive SAR image data associated with a target rockmass; and estimate water saturation of the target rockmass using the RDA, the phase tracking algorithm and the generated generalized calibration function, wherein the use of the RDA, the phase tracking algorithm, and the generated generalized calibration function ensure that the water saturation of the target rockmass is estimated without contacting the target rockmass.

8. The water saturated region detection system of claim 7, wherein for estimating the water saturation of the target rockmass using the RDA, the phase tracking algorithm and the generated generalized calibration function, the one or more hardware processors (204) are configured by the instructions to:

generate a target SAR complex image based on the received SAR image data using the RDA;

reconstruct a target 1D phase tracking signal using the phase tracking algorithm;

compute a peak unwrapped phase value for the target rockmass based on the target 1D phase tracking signal; and transform the peak unwrapped phase value into the water saturation using the generated generalized calibration function.

9. One or more non-transitory machine-readable information storage mediums comprising one or more instructions which when executed by one or more hardware processors cause:

receiving, by a water saturated region detection system (WSRDS), a synthetic aperture radar (SAR) data associated with a plurality of rock specimens, wherein the plurality of rock specimens comprises one or more of: a saturated-surface-dried (SSD) rock specimen, an oven-dried (OD) rock specimen, and an air-dried (AD) rock specimen;

generating, by the WSRDS, a SAR complex image based on the received SAR data using a range doppler algorithm (RDA), wherein the generated SAR complex image is a two-dimensional (2D) SAR complex image;

processing, by the WSRDS, the 2D SAR complex image using a phase tracking algorithm to obtain a one-dimensional (1D) phase tracking signal, wherein 1D phase tracking signal comprises topography information related to the plurality of rock specimens;

estimating, by the WSRDS, a peak unwrapped phase value for each rock specimen of the plurality of rock specimens based on the 1D phase tracking signal;

evaluating, by the WSRDS via the one or more hardware processors, a 3-point empirical polynomial function using the peak unwrapped phase value estimated for each rock specimen of the plurality of rock specimens; and generating, by the WSRDS, a generalized calibration function for water seepage mapping based, at least in part, on the 3-point empirical polynomial function using a gravimetric water saturation estimation procedure, wherein the generated generalized calibration function is used to detect water saturated regions in a target rockmass.

10. The one or more non-transitory machine-readable information storage mediums of claim 9, wherein the step of processing, by the WSRDS, the 2D SAR complex image using the phase tracking algorithm to obtain the 1D phase tracking signal comprises:

performing down-sampling of the 2D SAR complex image along a fast-time dimension by a predefined factor to obtain a down-sampled image;

applying a de-noising filter on the down-sampled image to obtain a de-noised down-sampled image, wherein the de-noised down-sampled image comprises one or more down-sampled signal values;

generating a 1D unwrapped phase tracking signal by taking mean of the one or more down-sampled signal values along the fast-time dimension; and obtaining the 1D phase tracking signal by applying a bandpass filter on the 1D unwrapped phase tracking signal in a predefined frequency range, wherein the use of the bandpass filter on the 1D unwrapped phase tracking signal ensures that residual noise is removed from the 1D unwrapped phase tracking signal.

11. The one or more non-transitory machine-readable information storage mediums of claim 9, wherein the one or more instructions which when executed by the one or more hardware processors further cause:

receiving, by the WSRDS, SAR image data associated with a target rockmass; and estimating, by the WSRDS, water saturation of the target rockmass using the RDA, the phase tracking algorithm and the generated generalized calibration function, and wherein the use of the RDA, the phase tracking algorithm, and the generated generalized calibration function ensure that the water saturation of the target rockmass is estimated without contacting the target rockmass.

12. The one or more non-transitory machine-readable information storage mediums of claim 11, wherein the step of estimating, by the WSRDS, the water saturation of the target rockmass using the RDA, the phase tracking algorithm and the generated generalized calibration function, comprises:

generating a target SAR complex image based on the received SAR image data using the RDA;

reconstructing a target 1D phase tracking signal using the phase tracking algorithm;

computing a peak unwrapped phase value for the target rockmass based on the target 1D phase tracking signal; and transforming the peak unwrapped phase value into the water saturation using the generated generalized calibration function.

* * * * *